United States Patent
Hicks et al.

(10) Patent No.: US 8,130,106 B1
(45) Date of Patent: *Mar. 6, 2012

(54) METHOD OF DETECTING SUGAR IN INDUSTRIAL PROCESS BOILER SYSTEMS

(75) Inventors: Peter D. Hicks, Aurora, IL (US); Jason S. Van't Hul, Harrisburg, SD (US)

(73) Assignee: Nalco Company, Naperville, IL (US)

( * ) Notice: Subject to any disclaimer, the term of this patent is extended or adjusted under 35 U.S.C. 154(b) by 10 days.

This patent is subject to a terminal disclaimer.

(21) Appl. No.: 12/465,342

(22) Filed: May 13, 2009

Related U.S. Application Data

(63) Continuation-in-part of application No. 12/262,581, filed on Oct. 31, 2008, now Pat. No. 8,068,033.

(51) Int. Cl.
 *G08B 21/00* (2006.01)
(52) U.S. Cl. ...................................... 340/603
(58) Field of Classification Search .................. 340/603, 340/540, 539.1, 286, 286.02; 210/696, 748.13; 422/7; 73/61.41
 See application file for complete search history.

(56) References Cited

U.S. PATENT DOCUMENTS

| | | |
|---|---|---|
| 4,269,717 A | 5/1981 | Slovinsky |
| 4,574,071 A | 3/1986 | DeSilva et al. |
| 4,648,043 A | 3/1987 | O'Leary |
| 4,775,005 A | 10/1988 | Beyer et al. |
| 4,830,757 A | 5/1989 | Lynch et al. |
| 5,236,845 A | 8/1993 | Pierce et al. |
| 5,238,846 A | 8/1993 | Aucutt |
| 5,243,297 A | 9/1993 | Perkins et al. |
| 5,268,092 A | 12/1993 | Eden |
| 5,332,494 A | 7/1994 | Eden et al. |
| 5,342,510 A | 8/1994 | Eden et al. |
| 5,348,664 A | 9/1994 | Kim et al. |
| 5,422,014 A | 6/1995 | Allen et al. |
| 5,470,484 A | 11/1995 | McNeel |
| 5,747,342 A * | 5/1998 | Zupanovich .................... 436/55 |

(Continued)

FOREIGN PATENT DOCUMENTS

JP 2003254503 9/2003

OTHER PUBLICATIONS

Buecker B., "Water Treatment: The Continuing Battle Against FAC," Power Engineering, Pennwell Publishing Co., Tulsa, OK, pp. 32-34, vol. 106, No. 9, Sep. 1, 2002.

Dedekind et al., "Oxygenated Feedwater Treatment at the World's Largest Fossil Fired Power Plant—Beware the Pitfall," Power Plant Chemistry, vol. 3, No. 11, Nov. 2001.

Filer, "Power Plant Chemistry Measurement Advancements: Oxidation Reduction Potential," Ultrapure Water, Nov. 1998.

(Continued)

*Primary Examiner* — Phung Nguyen
(74) *Attorney, Agent, or Firm* — Edward O. Yonter; Michael B. Martin

(57) ABSTRACT

This invention provides a method for detecting sugars in boiler condensate and/or boiler feedwater in industrial processes. The method includes measuring an oxidation-reduction potential at one or more locations in the process with one or more devices capable of measuring oxidation-reduction potential at operating temperature and pressure and correlating that measurement to an amount of sugar in the system. If the measured oxidation-reduction potential is not within an optimum range, action is taken.

17 Claims, 5 Drawing Sheets

U.S. PATENT DOCUMENTS

| | | | |
|---|---|---|---|
| 5,855,791 A | 1/1999 | Hays et al. | |
| 6,068,012 A | 5/2000 | Beardwood et al. | |
| 6,077,445 A | 6/2000 | Ascolese | |
| 6,336,058 B1 * | 1/2002 | Fowee | 700/266 |
| 6,350,376 B1 | 2/2002 | Imaoka et al. | |
| 6,391,256 B1 | 5/2002 | Moon et al. | |
| 6,402,984 B1 | 6/2002 | Nakajima et al. | |
| 6,409,926 B1 | 6/2002 | Martin | |
| 6,418,958 B1 * | 7/2002 | Rossi et al. | 137/93 |
| 6,436,711 B1 | 8/2002 | Davis et al. | |
| 6,566,139 B2 | 5/2003 | Davis et al. | |
| 6,587,753 B2 | 7/2003 | Fowee | |
| 6,609,070 B1 | 8/2003 | Lueck | |
| 6,620,315 B2 | 9/2003 | Martin | |
| 6,813,532 B2 | 11/2004 | Eryurek et al. | |
| 7,141,175 B2 | 11/2006 | Verma | |
| 7,208,117 B2 * | 4/2007 | Hays et al. | 422/3 |
| 2003/0004681 A1 | 1/2003 | Fandrich et al. | |
| 2006/0006122 A1 | 1/2006 | Burns et al. | |
| 2006/0169646 A1 | 8/2006 | Andree et al. | |
| 2006/0182651 A1 | 8/2006 | Bailey, III et al. | |
| 2008/0179179 A1 | 7/2008 | Hicks et al. | |
| 2008/0202553 A1 | 8/2008 | Hicks et al. | |

OTHER PUBLICATIONS

Haag, J. et al., "On-Line Measurement of Redox and Corrosion Potentials in Water for PWR Steam Generators," Kraftwerkstechnik, Kraftwerkstechnik GMbH, Essen, DE, pp. 236-241, vol. 70, No. 3, Mar. 1, 1990.

Niedrach, L. W., "Electrodes for Potential Measurements in Aqueous Systems at High Temperatures and Pressures," Angewandte Chemie—International Edition in English, pp. 161-169, vol. 26, No. 3, Mar. 1987.

Uchino et al., "Study on the Practical Application of a Method for Corrosion Potential Measurement in a Water Quality Monitoring System used During Combined Water Treatment," PowerPlant Chemistry, pp. 511-517, vol. 3, No. 9, 2001.

* cited by examiner

METHOD OF DETECTING SUGAR IN INDUSTRIAL PROCESS BOILER SYSTEMS

CROSS REFERENCE TO RELATED APPLICATION

This application is a continuation-in-part of U.S. patent application Ser. No. 12/262,581 filed Oct. 31, 2008, now U.S. Pat. No. 8,068,033, "Method of Detecting Contamination in Industrial Process Boiler Systems."

TECHNICAL FIELD

This invention relates generally to methods of detecting sugar in boiler condensate and/or boiler feedwater. More specifically, the invention relates to detecting sugar in boiler condensate and/or boiler feedwater in an industrial process.

BACKGROUND

Boiler condensate and feedwater contamination is an undesirable and frequently occurring problem in the fermentation industry and other industries. These contaminants contribute to system inefficiencies, corrosion, deposition, and other system issues. Particularly with boiler systems or other steam-generating systems, such issues result in detrimental effects on heat transfer and reduced asset life. Common contaminants in fermentation processes, for example, are wort and various types of sugars. In some cases, the presence of sugars is not necessarily contamination, but its detection and control is nonetheless desirable. Wort is a complex mixture that contains sugars that are fermented by brewing yeast to produce alcohol-containing product. Typical raw materials for its production include malted grain (e.g. barley) and water. In the beer brewing process it is sometimes referred to as hopped malt extract. Essentially this mixture is the basis for beer brewing and whiskey production processes.

Wort boiling is an essential step in beer brewing and whiskey production. It is a process by which hop components are extracted and transformed, including precipitation of proteins and conversion of dimethylsulfide to dimethylsulfoxide. During this process, the possibility exists, for example, of contaminating the boiler condensate due to direct steam contact with the product. Condensate contamination of the boiler feedwater might increase carryover from the boiler detrimentally resulting in organic acids in the steam and condensate system. Furthermore, steam purity is of the utmost importance to the industry due to possible contact of steam with the product and any contamination of the boiler or boiler water system compromises the entire operation.

Currently, measurement of wort and in particular sugar in condensate is performed with low frequency and using a well known laborious process. An example of such a system is disclosed in U.S. Pat. No. 5,238,846, titled "Method of Detecting the Presence of Sugar in Steam Generating Systems." The disclosed system includes detecting a colorimetric signal produced by exposing a grab sample with a reagent such as potassium permanganate and an acetate. Online measurement systems also exist; however, the devices used require high maintenance and are not considered robust.

There thus exists an industry need for improved methods of detecting amounts of sugar in boiler condensate and feedwater. A particular need exists for low maintenance, reliable, and automated methods of such detection.

SUMMARY

This invention accordingly provides a method for detecting sugar(s) in a boiler condensate and/or a boiler feedwater in industrial processes. Preferred industrial processes include those involving using, producing, or refining sugars and fermentation processes, such as beverage production (e.g., beer, whiskey, etc.) and industrial fermentation (e.g., ethanol, bio-ethanol, etc.). The method includes measuring an oxidation-reduction potential ("ORP") at one or more locations in the boiler condensate and/or the boiler feedwater of the process with one or more devices capable of measuring ORP at operating temperature and pressure (sometimes referred to herein as a "CSM device"). The CSM device is preferably in communication with a controller that is operable to assess whether the measured ORP or a calculated ORP based upon the measured ORP is within an optimum range and to correlate the measured ORP (or calculated ORP) to an amount of sugar present in the industrial process. In a preferred embodiment, an alarm or other indicator is triggered if the measured oxidation-reduction potential is not within an optimum range.

In an aspect, the method of the invention includes measuring an oxidation-reduction potential at one or more locations in the boiler condensate and/or boiler feedwater of the industrial process with one or more CSM devices. Process-side contaminants detrimentally affect normal boiler operations and are detectable and controllable using the method of the invention. Of particular concern is that these species can drastically lower the pH of boiler water if they find their way into operating boilers. If the measured oxidation-reduction potential is not within an optimum range, the method includes optionally triggering an alarm or other indicator/action so that corrective action (manual, mechanical, automatic, etc.) could be taken to limit the effects of the unwanted upset. Other indicators may include any type of signal or monitor that is operable, for example, to initiate a mechanism to stop or enable altering the operation of the industrial process. Such alterations will vary according to the particular indicator and application and will be determined by the operator or controller.

In another aspect, the invention is a system for detecting sugar(s) in boiler condensate and/or boiler feedwater in an industrial process. The system includes a controller in communication with at least one CSM device in a condensate stream derived from a steam generator. At least one chemical injection pump is optionally used to inject at least one reductant and/or pH-controlling chemical into a boiler feedwater and/or one or more satellite feed locations triggered by a signal received from the controller in relation to the measured ORP and operation of the chemical injection pump. The system may further include a condensate return line and a condensate discarding system (e.g., dump valve).

In an aspect, the method includes converting the measured oxidation-reduction potential into an input electrical signal capable of being transmitted to a controller and transmitting the input electrical signal to the controller. In a preferred aspect, the controller is operable to: (i) receive the transmitted input electrical signal; (ii) convert the received electrical signal into an input numerical value; (iii) analyze the input numerical value; (iv) generate an output numerical value: (v) convert the output numerical value into an output electrical signal; and (vi) transmit the output electrical signal.

In another aspect, the controller determines if the input numerical value is within an optimum range, and if the input numerical value is outside of the optimum range, the transmitted output electrical signal corresponding to the generated output numerical value triggers an alarm. In an embodiment, the method includes a mechanism to stop or alter the operation of the industrial process in the event of the alarm. In another embodiment, the method includes a mechanism to open or close one or more valves associated with the boiler condensate and/or a boiler feedwater or to cause other adjustments to the system as determined by the operator. One having ordinary skill in the art may determine the nature and degree of such adjustments.

In a further aspect, the invention includes a system for detecting sugar(s) in boiler condensate and/or boiler feedwater in a beverage fermentation process. The system includes a boiler or other steam generator; a beverage fermentor; an interface that forms a thermodynamic connection between the beverage fermentor and a steam and/or condensate stream derived from said boiler or steam generator; a condensate return line; a condensate storage tank; a condensate dump valve; a boiler makeup water source; and one or more at temperature and pressure oxidation reduction potential measuring devices.

It is an advantage of the invention to provide a precise, sensitive, and efficient method of reducing contamination of boiler condensate and/or boiler feedwater in industrial processes by measuring only the oxidation-reduction potential at operating temperature and pressure.

It is another advantage of the invention to provide a method of detecting amounts of sugar(s) and contaminants in boiler systems or steam-generating systems used in beverage fermentation processes.

It is a further advantage of the invention to maximize the volume and optimize the presence of chemical additives in condensate water that can be returned to the industrial process boiler as a feedwater source.

An additional advantage of the invention is to provide a robust method of optimizing condensate recycling to the boiler feedwater by measuring properties of the condensate water at operating temperature and pressure and incorporating these measurements into a feedback, feed-forward, or predictive control loop.

It is a further advantage of the invention is to provide a means of eliminating or reducing the lag time associated with conventional condensate measurement systems by enabling measurement of condensate properties at operating temperature and pressure.

An additional advantage of the invention is to provide optimized control over chemical additives being fed hereby minimizing the generation and return of corrosion by-product particles that threaten steam generator reliability and safety.

Still another advantage of the invention is to provide a method of measuring condensate properties online and in essentially real-time and possibly avoiding the cost of sample conditioning systems.

A further advantage of the invention is to reduce the potential safety and environmental risks resulting from contaminated condensate by minimizing the volume of discarded water.

It is yet another advantage of the invention to provide a method for determining and predicting the potential of engineering alloys (including iron and steel such as mild steel) to corrode in industrial process boiler systems.

Additional features and advantages are described herein, and will be apparent from, the following Detailed Description, Examples, and Figures.

DETAILED DESCRIPTION

Figure 1:
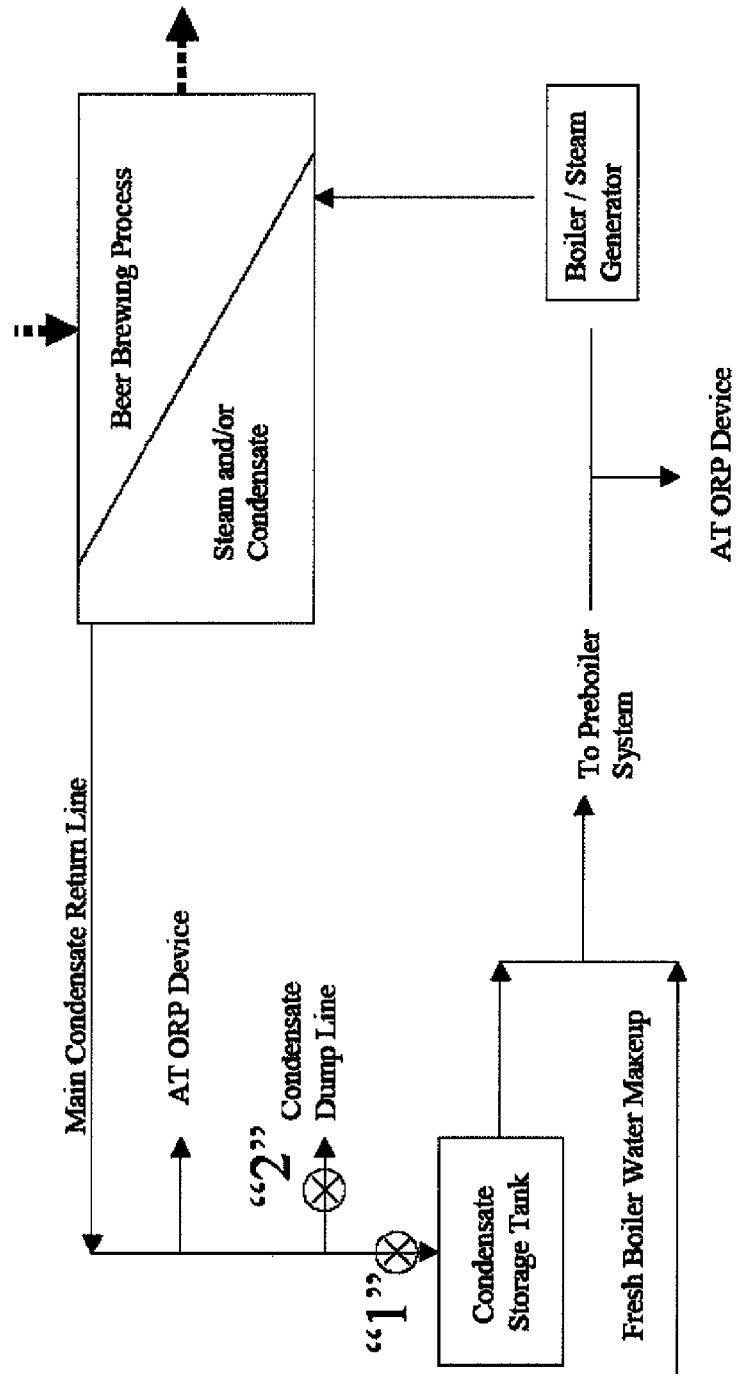
FIG. 1 shows an embodiment of the invention including two CSM devices installed in a beverage fermentation process.

"Boiler" refers to any hot water system or steam generator having a temperature from about 37° C. up to about 370° C. The hot water system may operate at or below atmospheric pressure or a pressure up to about 3,000 psi. A typical system has a water temperature of about 90° C. to about 260° C. and pressures reaching as high as about 3,000 psi.

"Condensate" refers to any system where typically boiler-created steam or process vapor (e.g., from an industrial process) has been condensed to liquid state. Condensate temperatures can vary from steam temperatures down to ambient temperatures. Typical water condensate temperature is about 80° C. (+/−about 30° C.).

"Controller," "controller system," and similar terms refer to a manual operator or an electronic device having components such as a processor, memory device, cathode ray tube, liquid crystal display, plasma display, touch screen, or other monitor, and/or other components. In certain instances, the controller may be operable for integration with one or more application-specific integrated circuits, programs, computer-executable instructions, or algorithms, one or more hard-wired devices, and/or one or more mechanical devices. Moreover, the controller is operable to integrate the feedback, feed-forward, or predictive loop(s) of the invention. Some or all of the controller system functions may be at a central location, such as a network server, for communication over a local area network, wide area network, wireless network, internet connection, microwave link, infrared link, and the like. In addition, other components such as a signal conditioner or system monitor may be included to facilitate signal-processing algorithms.

Preferably, the controller includes hierarchy logic to prioritize any measured or predicted properties associated with measured system parameters. For example, the controller may be programmed to prioritize ORP measurements received from certain parts of the system over others. It should be appreciated that the object of such hierarchy logic is to allow improved control over the system parameters and to avoid circular control loops.

In one embodiment, the method includes an automated controller. In another embodiment, the controller is manual or semi-manual. For example, where the industrial process includes one or more datasets received from various sensors in the system, the controller may either automatically determine which data points/datasets to further process or an operator may partially or fully make such a determination. A dataset from the industrial process, for instance, may include variables or system parameters such as oxidation-reduction potential, pH, levels of certain chemicals or ions (e.g., determined empirically, automatically, fluorescently, electrochemically, colorimetrically, measured directly, calculated), temperature, pressure, process stream flow rate, dissolved or suspended solids, etc. Such system parameters are typically measured with any type of suitable data capturing equipment, such as pH sensors, ion analyzers, temperature sensors, thermocouples, pressure sensors, corrosion probes, and/or any other suitable device or method. Data capturing equipment is preferably in communication with the controller and, according to alternative embodiments, may have advanced functions (including any part of the control algorithms described herein) imparted by the controller.

"Fermentation process" refers to any process including the fermentation of one or more sugars into alcohol. These processes include but are not limited to beer making processes, distillation process, industrial fermentation processes such as fuel ethanol or bioethanol. "Sugar" refers to any sugar or sugar-like substance, including but not limited to reducing sugars and non-reducing sugars. A reducing sugar is generally any sugar that forms an aldehyde or ketone in basic solution, which allows the sugar to act as a reducing agent. Monosaccharides and most disaccharides are typically reducing sugars, for example, glucose, fructose, glyceraldehyde, lactose, arabinose, dextrose, mannose, and maltose. Examples of non-reducing sugars include sucrose and trehalose. In some embodiments, sugars are considered contaminants (e.g., fermentation processes). In other embodiments, the detection and control of sugars is desirable, but they are not considered contaminants (e.g., sugar making processes).

"Hot water system" refers to any system where hot water is in contact with metallic or non-metallic surfaces in an industrial fermentation process. "Hot water" means water having a temperature from about 37° C. up to about 370° C. The hot water system may operate at or below atmospheric pressure or a pressure up to about 3,000 psi. A preferred hot water system is an industrial boiler system, which typically has a water temperature of about 90° C. to about 260° C. and pressures reaching as high as about 3,000 psi.

"Industrial process" refers to any process where a sugar source exists or where sugar may be encountered in condensate and/or feedwater, including but not limited to fermentation processes, grain wet milling, dry grind ethanol, and sugar making process such as sugar cane plants, and beet sugar plants.

"ORP," "ORP measurement," "measured ORP," or like terms refer to oxidation-reduction potential measurements taken at operating temperature and pressure (unless otherwise noted). In an embodiment, the term encompasses concurrently measured and relayed temperature signals.

"ORP device" refers to any device capable of measuring oxidation-reduction potential and is sometimes referred to herein as "CSM device" or "AT ORP device." According to alternative embodiments, the CSM device is operable to detect even minor variations in the level of system corrosion protection during normal operating periods, so that corrosion product generation is continuously minimized. The controller then determines whether any such variations require an adjustment to the chemical additives in the feedwater. Though any suitable device may be used to detect ORP as an indicator of the level of system corrosion protection, preferred devices include those disclosed in U.S. patent application Ser. Nos. 11/403,420, now U.S. Pat. No. 7,635,499, "Method of Inhibiting Corrosion in Hot Water Systems" and 11/668,048 and 12/114,288, "High Temperature and Pressure Oxidation-Reduction Potential Measuring and Monitoring Device for Hot Water Systems."

Signals produced by the ORP device may be used in accordance with the embodiments described herein and optionally in conjunction with any suitable method including the methods disclosed in the following commonly owned U.S. Patent Applications: "Method of Inhibiting Corrosion in Hot Water Systems," Ser. No. 11/403,420, now U.S. Pat. No. 7,635,499; "Method of Inhibiting Corrosion in Industrial Hot Water Systems by Monitoring and Controlling Oxidant/Reductant Feed Through a Nonlinear Control Algorithm," Ser. No. 11/692,542, now U.S. Pat. No. 7,666,312; "Method and Device for Creating and Analyzing an At Temperature and Pressure Oxidation-Reduction Potential Signature in Hot Water Systems for Preventing Corrosion," Ser. No. 11/782,246, now U.S. Pat. No. 7,955,853; "Method and Device for Preventing Corrosion in Hot Water Systems," Ser. No. 11/782,192; "Method and Device for Preventing Corrosion in Hot Water Systems Undergoing Intermittent Operations," Ser. No. 11/852,616, now U.S. Pat. No. 7,951,298; and "Method and Device for Cleanup and Deposit Removal from Internal Hot Water System Surfaces," Ser. No. 11/852,695, now U.S. Pat. No. 7,998,352.

Data transmission of measured parameters or signals to chemical pumps, alarms, or other system components is accomplished using any suitable device, such as a wired or wireless network, cable, digital subscriber line, internet, etc. Any suitable interface standard(s), such as an ethernet interface, wireless interface (e.g., IEEE 802.11a/b/g/x, 802.16, Bluetooth, optical, infrared, radiofrequency, etc.), universal serial bus, telephone network, the like, and combinations of such interfaces/connections may be used. As used herein, the term "network" encompasses all of these data transmission methods. Any of the described devices (e.g., plant archiving system, data analysis station, data capture device, process station, etc.) may be connected to one another using the above-described or other suitable interface or connection.

In an embodiment, system parameter information is received from the system and archived. In another embodiment, system parameter information is processed according to a timetable or schedule. In a further embodiment, system parameter information is immediately processed in real-time/substantially real-time. Such real-time reception may include, for example, "streaming data" over a computer network.

This invention also provides a novel method of managing condensate streams associated with industrial processes through the use of a CSM in conjunction with a controller (as described below). The invention has particular utility in its capability of minimizing corrosion in condensate systems of hot water systems, with specific benefits to fermentation processes and the detection of sugar(s). In a preferred embodiment, the CSM is operable to measure the oxidation-reduction potential at operating temperature and pressure (such measurements are sometimes referred to herein as "ORP"). In conjunction with a controller system, a CSM installed on a flowing or offline condensate stream detects the condition of the metal in the system to optimize the application of both passivating and online chemical additive treatment programs. The scope of the method includes the ability to generate reliable condensate stream data and use that data in a feedback, feed-forward, or predictive loop(s) to make real-time adjustments to chemical additive treatments thus increasing the quality of the feedwater.

In a preferred embodiment, the invention is implemented to provide continuous or intermittent feedback, feed-forward, or predictive information to process chemical injection pumps or valves to make real-time adjustments. The invention incorporates programming logic to convert analyzer signals to pump/valve adjustment logic and, in a preferred embodiment, controls one or each of a plurality of chemical injections with a unique basis. It is also envisioned that the invention may also manage and integrate readings from existing electrical resistance corrosion probes, linear polarization probes, and/or other techniques for measuring metal loss. In an embodiment, these readings will be programmed through, for example, a Programming Logic Controller (PLC) to possibly override or modify the other chemical inputs and change pump rates.

When downtime conditions occur, the CSM is capable of optimizing the feed of passivating treatment, which allows for online sensing of the metal condition as a result of the water chemistry present. If, as would be the case when the condensate contains some oxygen as a result of the downtime conditions, the CSM would sense this condition and the controller component would send a signal to one or more chemical injection pumps to increase the dosing of the chemical additives (e.g., combined reducing agent/amine) to restore protective conditions to minimize corrosion.

Such additives may include changes and adjustments to feedwater, satellite feeding location, and/or steam condensate chemistry. For example, the changes may include adding oxygen or one or more oxygen scavengers to the feedwater, satellite feeding location, and/or steam condensate. By definition, oxygen scavengers are reducing agents (reductants), although not all reducing agents are necessarily oxygen scavengers. For practical applications, reasonable reactivity is required at low temperatures. That is, there should be some favorable kinetics of reaction. Furthermore, other changes and adjustments to the system water chemistry, such as for system control and corrosion control, may include adding other oxidizing agents (oxidants) or other reducing agents (reductants).

Preferably, the present invention includes adjusting the chemical additives based on amount of reducing agent added to the feedwater, satellite feeding location, and/or steam condensate. The term "reductant" refers to any chemical capable of reacting as a reducing agent. Representative non-limiting examples of reductants include hydrazine, sulfite, carbohydrazide, N,N-diethylhydroxylamine, hydroquinone, erythorbate, methyl ethyl ketoxime, hydroxylamine, tartronic acid, ethoxyquin, methyltetrazone, tetramethylphenylenediamine, semi-carbazides, diethylaminoethanal, 2-ketogluconate, N-isopropylhydroxylamine, ascorbic acid, gallic acid, and hydroxyacetone.

In at least one embodiment, the invention includes controlling an amount of pH-controlling chemical added to the feedwater or satellite feeding site. "pH-controlling chemical" means any suitable chemical or compound that, when added to a solution, composition, and/or formulation, is capable of adjusting pH, controlling pH, and/or maintaining pH. Representative pH-controlling chemicals include ammonia and amines, such as cyclohexamine, morpholine, diethylaminoethanol (DEAE), methoxypropylamine, monoethanolamine, the like, and combinations thereof.

Though condensate sampling (via online exposure to the CSM) may occur at any point in the flow path, the ORP of the condensate at the end of the process flow path is typically indicative of the chemical conditions in the system. System turnover is generally at a sufficient rate such that the dosage being fed would not be excessive during these conditions, plus the application of additional chemical feed can be managed by careful selection of the size of the injection pump. Preferably, the CSM is exposed to a liquid stream that is representative of the performance in the entire system. Typically, such exposure takes place at the beginning of a particular phase in the system, rather than further downstream. Ideal exposure takes place in a flowing sample stream that is well-mixed. It should, however, be understood that the CSM may be located at any suitable location.

Referring to FIG. 1, an embodiment of the invention including two CSM devices installed in a beverage fermentation process is shown. The boiler or steam generator provides a source of steam for the industrial process, such as a beer brewing process. Heat is transferred from the steam to the process via the thermodynamic connection between these two systems. Such heat transfer systems are well known in the art and further explanation is beyond the scope of this invention. It should be appreciated, however, that any boiler system or other suitable steam generating apparatus may be used with this invention. The arrow labeled "Main Condensate Return Line" directs condensate to the "Condensate Storage Tank." The condensate then combines with a source of "Fresh Boiler Water Makeup" and to the "Preboiler System" to provide additional water as needed for further steam generation.

In this embodiment, two CSM devices are installed in the system. The first CSM device is installed in the main condensate return line and the second is installed between the preboiler system and the boiler or steam generator. In one embodiment, the system includes valves, labeled "1" (valve leading to the condensate storage tank) and "2" (valve leading to the "Condensate Dump Line") in FIG. 1. The valves may either be automatically or manually adjusted (i.e., opened or closed, either completely or partially) in response to measured ORP signals.

For example, if the measured ORP signal is not within a predetermined optimum value, it may require that the condensate tank receive a smaller amount of condensate from the main condensate return line, valve "2" may be opened to release a portion of the condensate from the condensate return line via the condensate dump line. A portion or all of the condensate water may be discarded and compensated with water from a makeup water source to keep boiler feedwater ORP values within acceptable limits. Such limits typically depend upon the particular metallurgy of the system, operational parameters, etc. and are determined during a monitoring or testing period.

In an embodiment, the CSM devices monitor fluctuations in the condensate system. Such fluctuations provide information to aid in predicting possible problems in the system, such as in the full spectrum of mechanical, operational, and chemical use of the steam generating system and its components.

In an embodiment, one or more CSM devices are in contact with the boiler condensate and/or boiler feedwater. The boiler condensate may include one or both of boiler condensate return line(s) and boiler condensate storage tank.

In alternative embodiments, the method may be operated continuously, automatically, intermittently, and/or online.

The foregoing may be better understood by reference to the following examples, which are intended for illustrative purposes and are not intended to limit the scope of the invention.

Figure 2:
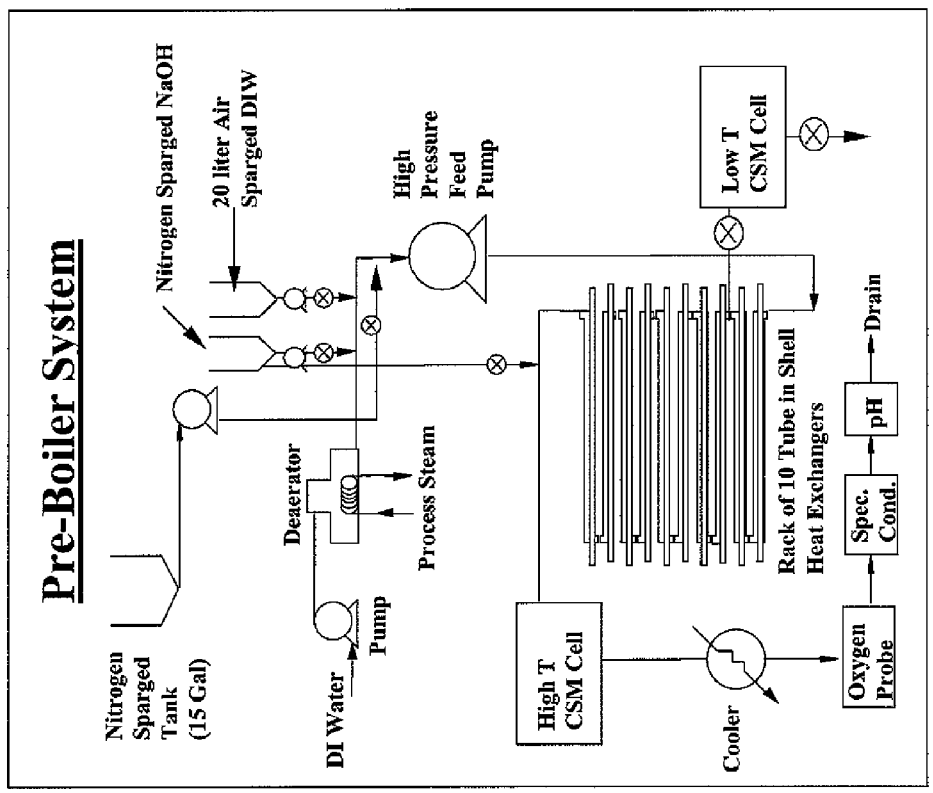
FIG. 2 illustrates a schematic of the preboiler simulator (PBS) rig used for testing in the examples.

Referring to FIG. 2, tests were run in the illustrated preboiler simulator (PBS). Feedwater flows from the "Deaerator" to the dosing station (comprised of "Nitrogen Sparged NaOH" and "20 liter Air Sparged DIW"). The "High Pressure Feed Pump" pumps the feedwater into the "Rack of 10 Tube in Shell Heat Exchangers." These heat exchangers function to heat incoming water from about 68° F. at the heater rack inlet to about 180° F. at the High T CSM Cell. Total system flow was about 525 ml/min for this series of tests. The pressure in the PBS rack, after the main feedwater pump, is about 900 psi. The Deaerator drop leg temperature was 225° F., and the water was then immediately cooled to 68° F. CSM devices were placed after heater position number 2 and number 10 (shown as "High T CSM Cell" and "Low T CSM Cell" in FIG. 2, meaning high temperature and low temperature, respectively). Water was then cooled and depressurized before passing through an analytical rack and finally dumped to drain.

About 120 ml/min was extracted from the main water flow of 525 ml/min as water was passed through the Low T CSM Cell and discarded to drain. The remainder of the water flowed through the High T CSM Cell. After the water was cooled and depressurized it was split into two streams. One stream of about 120 ml/min flowed through the sample section for room temperature (RT) water chemistry analysis and the rest was dumped to drain. The addition of chemistry to the inlet of the main FW pump was detected by Low T CSM cell after about 2 minutes and by High T CSM Cell after about 6 minutes, based on flowrates and rig volumes.

The goal for the below tests was to get the temperature at the Low T CSM cell to be as close to 77° F. as possible and the temperature in the High T CSM Cell to about 180° F. The 180° F. temperature was used as the critical temperature to simulate condensate temperatures in actual system operation. The 77° F. temperature was used to simulate typical room temperature ORP conditions. The same CSM device design was used in both cases, but the temperature of the water flowing through each cell was different.

Chemistries added and the feed tank makeup procedures were as follows. The caustic tank was made up with 1.24 g 50% NaOH in 20 liters and pumped in at 15% stroke on a mini LMI pump (about 1 ml/min). As such, a pH of about 8.2 (at 77° F.) was maintained. The specific conductivity was about 0.3 to 0.4 microS/cm (at 77° F.). There were two major test series run. In the first test series the sugars were added to an air saturated tank in various concentrations and fed into the PBS rig at the point of caustic injection, at a fixed rate. In test series number two, a fixed concentration of sugar was made-up in the 15-gallon nitrogen-sparged make-up tank. This solution was fed at various different feed rates into the PBS system. By running these two series of tests, the effect of dissolved oxygen baseline (varying redox stress) and sugar addition was determined. In particular, fructose and dextrose levels were analyzed.

For Examples 1 to 3 below, the pH was 8.2 (at 77° F.) for the 180° F. tests and the specific conductivity was 0.3 to 0.4 microS/cm. For the 266° F. tests of Example 3, the pH was 9.2 (at 77° F.) and the specific conductivity was 3 to 4 microS/cm. In all cases, the pH was caustic-adjusted.

Example 1

Figure 3:
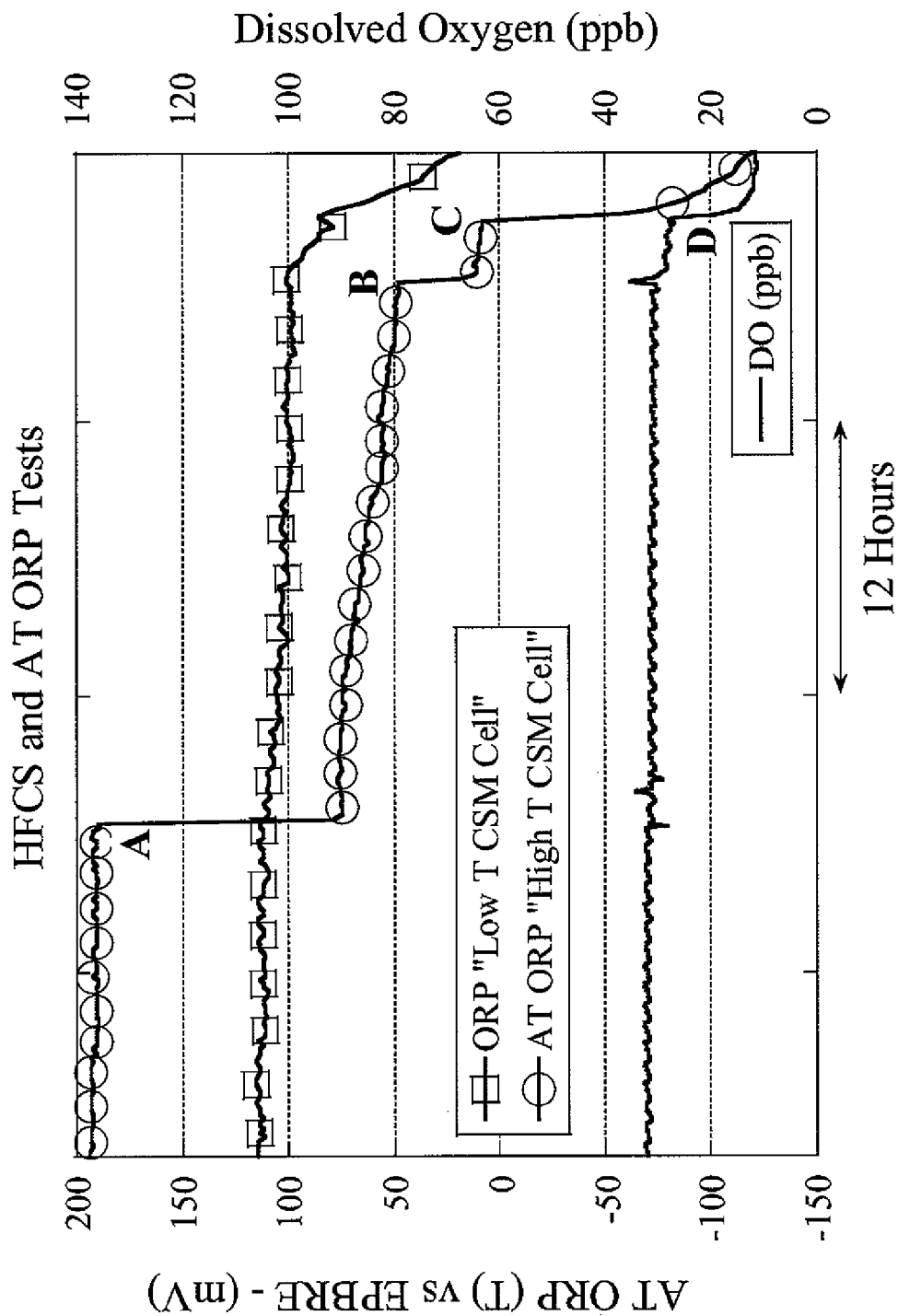
FIG. 3 shows ORP responses to adding increasing amounts of high fructose corn syrup (HFCS) to the elevated dissolved oxygen (DO) background PBS feedwater, as explained in Example 1.
Figure 4:
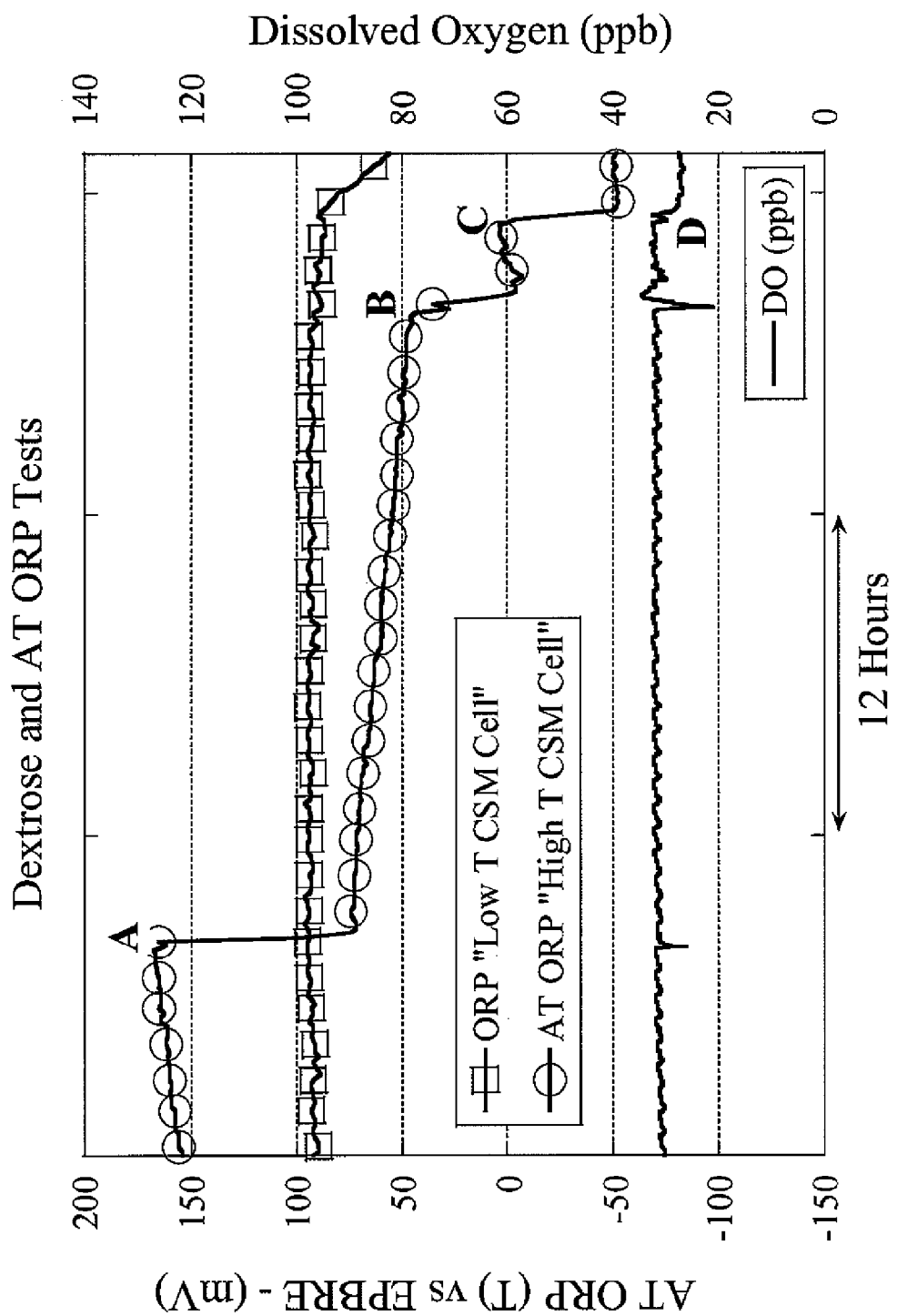
FIG. 4 shows ORP responses to adding increasing amounts of dextrose to elevated DO background PBS feedwater.
Figure 5:
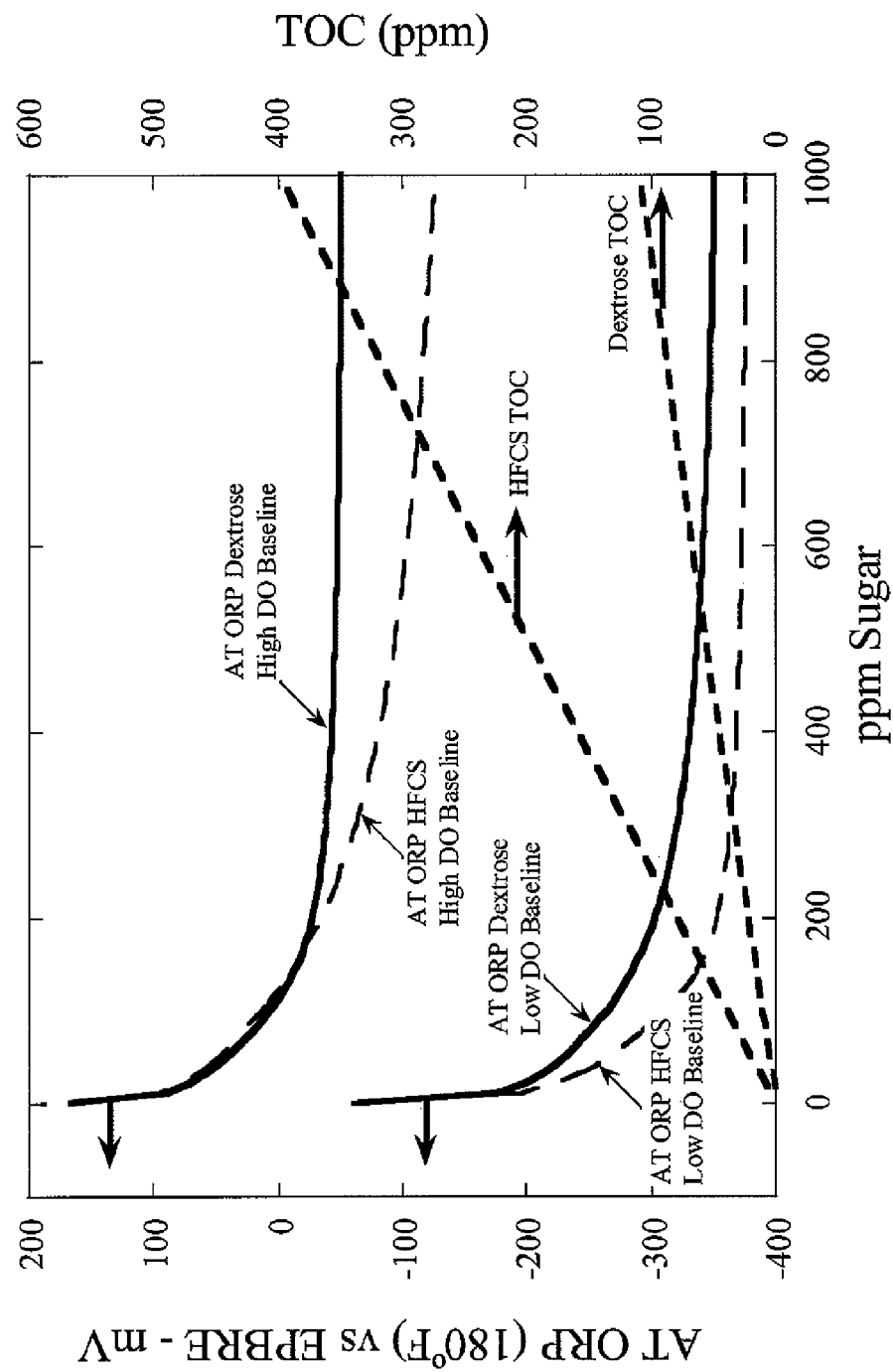
FIG. 5 shows combined data for high temperature ORP and total organic carbon (TOC) data taken for the dextrose and HFCS tests in the examples.

The baseline conditions during this test series were to feed air sparged DIW (de-ionized water) at the same location as the caustic (see the 20 liter tank addition point FIG. 2). In this case, the feed rate was at 20% stroke (about 2 ml/min) on the same LMI pump (2nd Pump head) as for the caustic additions. This was to provide a dissolved oxygen (DO) value of greater than 30 ppb at the High T CSM Cell position. For the case of chemical addition, the sugars were added to the Air Sparged DIW tank (as in FIG. 2). The sugars (high fructose corn syrup (HFCS) and dextrose) were initially added in small concentrations, followed by increasing concentrations. Results are shown in FIGS. 3 and 4 for the HFCS and dextrose tests, respectively. "AT ORP" refers to high temperature ORP measurements in all figures. Point A in FIG. 3 indicates 10 ppm HFCS feed; Point B indicates the start of 100 ppm HFCS feed; and Point C indicates the start of the 1,000 ppm HFCS feed. The same ppm levels of dextrose are also shown in FIG. 4, with the "A," "B," and "C" designations. Concentrations were calculated using the volume of liquid in the 20-liter supply tank and the system flowrates. CSM data is given as AT ORP data taken at the quoted temperature and versus the EPBRE (external pressure balanced reference electrode). Also presented (in FIG. 5) are the total organic carbon (TOC) data for all tests run. The TOC limit of detection was 2 ppm for the specific analytical technique used here. The CSM results from FIGS. 3 and 4 are shown in FIG. 5 as the "High DO Baseline" results.

Example 2

Prior to feeding chemistry into the system, several gallons of chemistry were prepared and vigorously nitrogen sparged for over an hour. For both sugars the 1,000 ppm tests were run first for several hours, followed by the 100 ppm tests for a longer time period. The 1% feed rate tests were run overnight. In this case, the dose rate of the chemistry was varied across 3 orders of magnitude. The same concentration of sugar was present in the makeup tank at all times. Pump flowrates were set at 1, 10, and 100% feed rates on an LMI dose pump to correspond to the 10, 100, and 1,000 ppm of sugar chemistry actives feedrates. Data from these "Low DO Baseline" tests are also shown in FIG. 5.

Examples 1 and 2 cover the HFCS and dextrose tests run with the higher, and then lower, DO baseline conditions, respectively. All tests clearly showed that the sugars are easily detected by the High T CSM Cell (i.e., 180° F. CSM device). The 77° F. (or room temperature) data shows that ORP measured at lower temperature lacks the sensitivity to pick up the marked changes seen by the higher temperature CSM measurements, as illustrated in FIGS. 3 and 4. Particularly, point D in FIG. 3 shows that the DO declined for the 1,000 ppm HFCS feed test. Although a portion of the observed decline may have been associated with other factors (e.g., difficulties in pumping high viscosity sugar solutions), TOC results clearly showed that HFCS was entering the system.

It should be noted that the ORP declines were primarily due to the presence of the HFCS and dextrose, and not their mild oxygen scavenging properties. Both sugars are reductants and were detected by high temperature ORP measurements. FIGS. 3 and 4 likewise clearly show the immediate step function response (lowering) of the high temperature ORP reading as more sugar was fed to the system. The chemical addition was immediately noticed. Point D in FIG. 4 shows that dextrose may also act as a mild scavenger (see the DO decline for very high dextrose additions). FIG. 5 shows additional high temperature ORP data for the above examples. The lines in FIG. 5 are smoothed best-fit lines through the data generated above and is a combination plot including the AT ORP and TOC data. FIG. 5 also includes the dextrose and HFCS tests run with lower DO baseline conditions, together with TOC data.

Example 3

While fructose and dextrose are generally known as "reducing" sugars, their dramatic effect on AT ORP was not known prior to the above high temperature studies. In a similar test to that shown for FIGS. 3 and 4, sucrose (a "non-reducing" sugar) was added at the 100 ppm level. As a non-reducing sugar, sucrose additions would not be expected to have a profound effect on CSM values; however, such an effect was observed.

The 100 ppm sugar addition test and the AT ORP decline for the high DO baseline comparison is shown in the table below. In addition, the 100 ppm sucrose sugar test was also run at higher temperatures (266° F.), which data is also given in the table below. All AT ORP values taken with the CSM device are given as versus the EPBRE (described in one or more of the U.S. patent applications cited above) in millivolts.

| 100 ppm Sugar (at 180° F.) | Fructose | Dextrose | Sucrose | Sucrose (at 266° F.) |
|---|---|---|---|---|
| AT ORP (mV) | 12 | 4 | 75 | −220 |
| AT ORP decline on adding the 100 ppm sugar (mV) | 173 | 181 | 110 | 363 |

For the 180° F. (in "High T CSM Cell" position in FIG. 2) test, it can be seen that the decline in AT ORP for sucrose is the lowest of the 3 sugars tested (110 mV), but the decline was measureable and significant. The 266° F. (in "High T CSM Cell" position in FIG. 2) decline in AT ORP of 363 mV was dramatic and unexpected for sucrose. Not intending to be bound by a particular theory, sucrose decomposition is typically a function of pH, time, temperature, salt and metal presence, etc. Any combination of these factors may contribute to converting a non-reducing sugar such as sucrose into components detectable via the CSM. Generally, pH less than 9 or greater than 9, more time, higher temperatures, and higher salts/metals may increase detection. Even with regard to these factors, within the 6-minute residence in the PBS rig, one would expect only an about 0.1% degradation of sucrose.

While this invention may be embodied in many different forms, there are described in detail herein specific preferred embodiments of the invention. The present disclosure is an exemplification of the principles of the invention and is not intended to limit the invention to the particular embodiments illustrated. Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A method for detecting sugar(s) in a boiler condensate and/or a boiler feedwater in an industrial process, the method comprising:
   (a) measuring an oxidation-reduction potential ("ORP") at one or more locations with one or more devices in contact with the boiler condensate and/or the boiler feedwater of the industrial process at operating temperature and pressure ("CSM device"), wherein the CSM device is operable to communicate with a controller;
   (b) transmitting the measured ORP to the controller;
   (c) correlating the measured ORP to an amount of sugar present in the industrial process;
   (d) assessing whether the measured ORP or a calculated ORP based upon the measured ORP is within an optimum range; and
   (e) triggering an alarm or other indicator/action if the measured ORP is not within the optimum range.

2. The method of claim 1, wherein the industrial process is a fermentation process.

3. The method of claim 1, wherein the industrial process is selected from the group consisting of: grain wet milling, dry grind ethanol, and sugar making.

4. The method of claim 1, including converting the measured oxidation reduction potential into an input electrical signal capable of being transmitted to a controller and transmitting the input electrical signal to the controller.

5. The method of claim 4, including determining if the input numerical value is within the optimum range, and if the input numerical value is outside of the optimum range, the transmitted output electrical signal corresponding to the generated output numerical value triggering the alarm.

6. The method of claim 1, wherein the controller is operable to: (i) receive the transmitted input electrical signal; (ii) convert the received electrical signal into an input numerical value; (iii) analyze the input numerical value; (iv) generate an output numerical value: (v) convert the output numerical value into an output electrical signal; and (vi) transmit the output electrical signal.

7. The method of claim 1, wherein the boiler condensate includes a boiler condensate return line and/or a boiler condensate storage tank.

8. The method of claim 1, wherein the one or more installed CSM devices are in contact with the boiler condensate and/or the boiler feedwater.

9. The method of claim 1, including transmitting the input electrical signal and/or the output electrical signal wirelessly.

10. The method of claim 1, wherein the optimum range is user-defined.

11. The method of claim 1, including operating the method continuously, automatically, and/or online.

12. The method of claim 1, including operating the method intermittently.

13. The method of claim 1, including a mechanism to open or close one or more valves associated with the boiler condensate and/or a boiler feedwater.

14. The method of claim 1, including operating the method over a network.

15. A digital storage medium having computer-executable instructions stored thereon, the instructions operable to execute the method of claim 1.

16. A system for detecting sugar(s) in boiler condensate and/or boiler feedwater in a beverage fermentation process, the system comprising: a boiler or other steam generator at operating temperature and pressure; a beverage fermentor; an interface that forms a thermodynamic connection between the beverage fermentor and a steam and/or condensate stream derived from said boiler or steam generator; a condensate return line; a condensate storage tank; a condensate dump valve; a boiler makeup water source; and one or more at temperature and pressure oxidation reduction potential measuring devices.

17. A system for detecting sugar(s) in boiler condensate and/or boiler feedwater in an industrial process, the system comprising: a boiler or other steam generator at operating temperature and pressure; a sugar source; a condensate return line; and one or more at temperature and pressure oxidation reduction potential measuring devices.

* * * * *